(12) United States Patent
Bell et al.

(10) Patent No.: US 7,741,266 B2
(45) Date of Patent: Jun. 22, 2010

(54) PROCESS FOR PREPARING SCENTED CELLULOSICS AND PRODUCTS PREPARED THEREBY

(75) Inventors: Adam Bell, Short Hills, NJ (US); Mohamed Mohamed, Edison, NJ (US); Robert Zwick, Chatham, NJ (US); James Bumenfeld, Lincroft, NJ (US)

(73) Assignee: Rotuba Extruders, Inc., Linden, NJ (US)

( * ) Notice: Subject to any disclaimer, the term of this patent is extended or adjusted under 35 U.S.C. 154(b) by 919 days.

(21) Appl. No.: 11/307,758

(22) Filed: Feb. 21, 2006

(65) Prior Publication Data

US 2006/0104933 A1     May 18, 2006

Related U.S. Application Data

(60) Provisional application No. 60/692,644, filed on Jun. 20, 2005, provisional application No. 60/705,807, filed on Aug. 4, 2005, provisional application No. 60/739,304, filed on Nov. 23, 2005.

(51) Int. Cl.
*A61Q 13/00* (2006.01)
*C11D 3/50* (2006.01)
*C11B 15/00* (2006.01)

(52) U.S. Cl. .............................. 512/1; 512/4
(58) Field of Classification Search ....... 512/1
See application file for complete search history.

(56) References Cited

U.S. PATENT DOCUMENTS

| | | | |
|---|---|---|---|
| 2,169,055 A * | 8/1939 | Overshiner | 239/54 |
| 3,261,746 A * | 7/1966 | Copley | 424/416 |
| 3,661,838 A | 5/1972 | Enomoto | |
| 3,800,124 A | 3/1974 | Walsh | |
| 4,044,231 A | 8/1977 | Beck et al. | |
| 4,476,171 A * | 10/1984 | Takeuchi | 428/38 |
| 4,492,644 A | 1/1985 | Matsumoto | |
| 4,598,006 A | 7/1986 | Sand | |
| 5,202,114 A | 4/1993 | Ogusu et al. | |
| 5,460,787 A | 10/1995 | Colon | |
| 5,846,607 A * | 12/1998 | Hurley et al. | 427/374.2 |
| 6,057,015 A | 5/2000 | Blum et al. | |
| 6,132,830 A | 10/2000 | O'Halloran | |
| 6,139,822 A * | 10/2000 | Socci et al. | 424/61 |
| 6,402,040 B1 | 6/2002 | Boyd et al. | |
| 6,542,217 B2 | 4/2003 | Boyd et al. | |
| 6,703,012 B1 | 3/2004 | White | |
| 7,182,451 B2 | 2/2007 | Auslander | |
| 7,200,363 B2 | 4/2007 | Greco et al. | |
| 2003/0072733 A1 | 4/2003 | McGee et al. | |
| 2006/0165622 A1* | 7/2006 | Hiramoto et al. | 424/65 |

FOREIGN PATENT DOCUMENTS

| | | |
|---|---|---|
| EP | 1424917 A1 | 6/2000 |
| GB | 2417709 A | 3/2006 |
| JP | 03-243669 | * 10/1991 |
| JP | 03-243669 | * 10/1991 |
| JP | 11178909 A | 12/1997 |
| WO | 9725087 | 7/1997 |

OTHER PUBLICATIONS

International Search Report and Written Opinion of the International Searching Authority for PCT/US06/06399 issued Jul. 11, 2008 (6 sheets).

* cited by examiner

*Primary Examiner*—James Seidleck
*Assistant Examiner*—Saira Haider
(74) *Attorney, Agent, or Firm*—Leason Ellis LLP

(57) ABSTRACT

The present invention provides a process for optimizing the fragrance of a scented cellulosic.

9 Claims, 1 Drawing Sheet

US 7,741,266 B2

PROCESS FOR PREPARING SCENTED CELLULOSICS AND PRODUCTS PREPARED THEREBY

This application claims the benefit of U.S. Provisional Application No. 60/739,304, filed Nov. 23, 2005, U.S. Provisional Application No. 60/705,807, filed Aug. 4, 2005, and U.S. Provisional Application No. 60/692,644, filed Jun. 20, 2005. Each of these applications are hereby incorporated by reference in their entirety.

FIELD OF THE INVENTION

The present application provides scented cellulosics that can be used for various end-use applications including, personal accessories, scented point-of-purchase applications, and promotional items for fine fragrances.

BACKGROUND OF THE INVENTION

Various applications that employ plastics (e.g., cellulosics) could be enhanced if the plastics could exude a pleasing or appropriate fragrance based on their end use.

U.S. Pat. No. 5,460,787 discloses a scented card which includes a fragranced thermoplastic material. The process of producing the scented card includes, providing a dry particulate thermoplastic material, blending a chemical flowing agent and at least one fragrance into the thermoplastic material to form a mixture, and heating the mixture in a thermoplastic extruder. The chemical flowing agent creates gas pockets within which the fragrance is trapped.

U.S. Pat. No. 3,661,838 discloses a scented plastic composition having a porous, finely divided silica powder having absorbed thereon a liquid scent emitting substance that is contained within the plastic material. The patent states that previous attempts have been made to dissolve a liquid scent-emitting substance into the liquid plasticizer, and a mixture of the scent emitting substance and plasticizer is subsequently added to the resin followed by heating and solidification. According to the patent, the liquid scent emitting substances which are dissolved in the plasticizers under known processes evaporate or decompose due to the processing heat applied during the time of the heat melting process, and do not provide sufficient fragrance intensity.

U.S. Published Patent Application No. 2003/0072733 discloses cellulose acetates as absorbent materials in a process for absorbing moisture and/or malodor in providing a fragrance to the surrounding ambience. The cellulose acetate and cellulose butyrate is not plasticized nor is a process provided for providing a fragrance plastic product.

U.S. Pat. No. 6,703,012 discloses compositions containing fragrances and powdered water-soluble polymers that are processed into toilet blocks. Polyvinyl acetates and mixtures of polyvinyl alcohol in partially hydrolyzed polyvinyl acetate are used. The fragrance is introduced into the extruder and the time of extruding the polymer.

U.S. Pat. No. 4,492,644 discloses and ethylene and vinyl acetate copolymer used with a perfume. The ethylene-vinyl acetate copolymer is pre-formed into granules having a diameter of about one to ten millimeters. A perfume and granulated copolymer are mixed at a temperature in a range of about ten degrees Celsius. This patent states that the granulated ethylene-vinyl acetate copolymer containing the perfume may increase in volume according to the amount of the perfume impregnated and absorbed therein, but it will never exhibit a softening effect. The '644 patent is not directed to cellulose acetate esters, such as cellulose acetate, cellulose acetate butyrate, and cellulose acetate propionate.

U.S. Pat. No. 4,598,006 discloses a method for impregnating a thermoplastic polymer with a fragrance by dissolving the fragrance in a volatile swelling agent maintained at or near super-critical conditions for the volatile swelling agent, swelling the thermoplastic polymer by contacting it at or near the supercritical conditions of the volatile swelling agent, then reducing the pressure so that the volatile swelling agent diffuses out of the thus impregnated thermo-plastic polymer. The thermoplastic polymer swells upon contact with the fragrance at or near supercritical conditions. The contacting permits rapid diffusion of the impregnation material into the polymer. Swelling agents include carbon dioxide, ethylene and nitrous oxide.

There is a need for imparting fragrance to cellulosics, including cellulose acetate, cellulose acetate butyrate, and cellulose acetate propionate, that has sufficient fragrance intensity while minimizing the amount of fragrance used, and also avoids compromising the plastic by the addition of silica materials or the addition of extraneous components to create formation voids within the plastic. There is a further need to optimize the fragrance of a cellulosic either by process improvements or additives so that end-use products that are made of the fragranced cellulosic have an optimal fragrance amount and are appealing to the consumer.

BRIEF SUMMARY OF INVENTION

The present application provides a process for preparing scented cellulosic with optimal fragrance intensity, including the steps of determining an amount of net plasticizer to be added to a pre-melt cellulosic composition; selecting a high preliminary fragrance:plasticizer weight ratio of the net plasticizer; adding the net plasticizer with the high preliminary fragrance:plasticizer ratio; determining the fragrance:plasticizer weight ratio of net plasticizer that achieves maximum fragrance intensity in the processed scented cellulosic by decreasing the fragrance:plasticizer ratio of the net plasticizer in iterative trials; and selecting a final fragrance:plasticizer ratio based on the desired fragrance intensity of the scented cellulosic, whereby the final fragrance:plasticizer ratio is less than or equal to the fragrance:plasticizer ratio that achieves the maximum fragrance intensity.

The present invention also provides a scented cellulosic composition comprising a cellulosic, a plasticizer, a fragrance component, and a solvent system that comprises a component that has both a non-polar and polar character. In one embodiment, the solvent system comprises, or consists essentially of, a glycol or a glycol ether, such as but not limited to, hexylene glycol, propylene glycol, butyl carbitol, 2-butoxyethanol (ethylene glycol mono-n-butyl ether) or pentyl ethylene glycol. In a preferred embodiment, the solvent system comprises hexylene glycol.

DETAILED DESCRIPTION

Definitions

Figure 1:
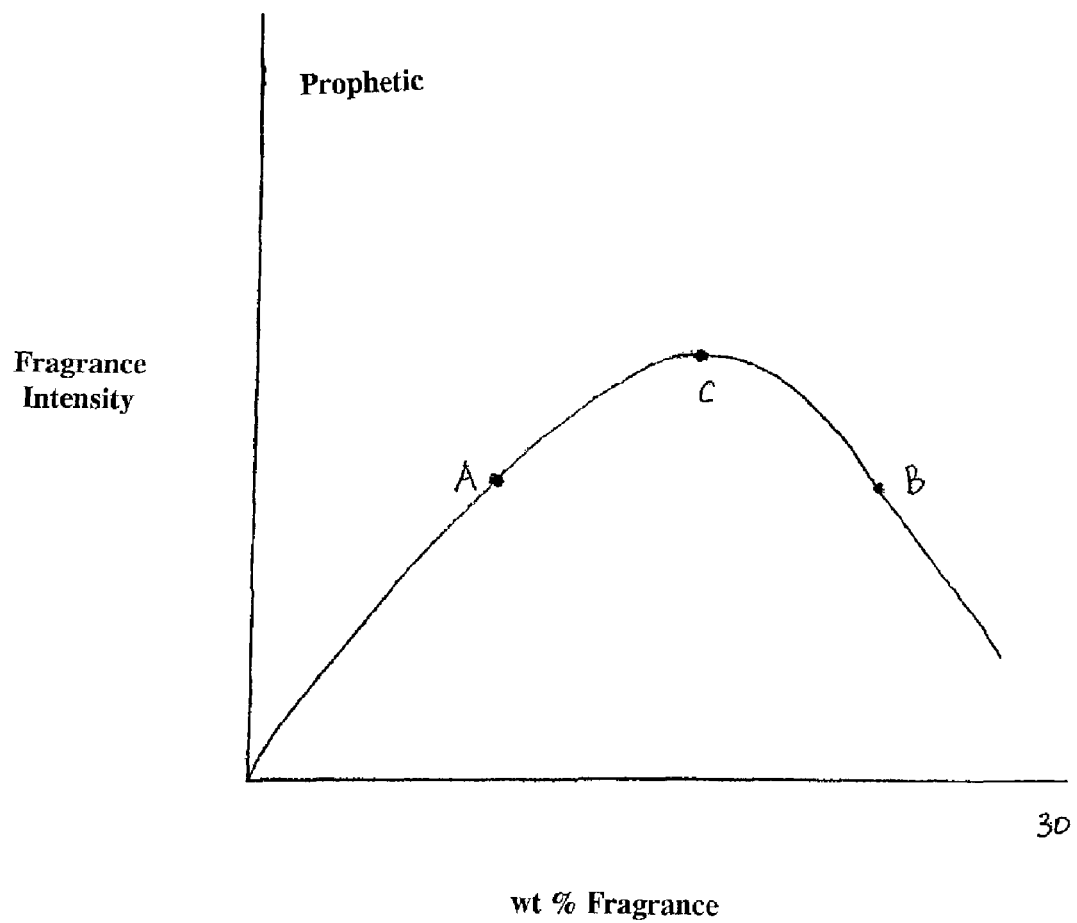
FIG. 1 is a conceptual drawing of the fragrance profile of a scented cellulosic having varying weight ratios of fragrance: plasticizer.

As used herein and in the appended claims, the singular forms "a," "an," and "the," include plural referents unless the context clearly indicates otherwise. Thus, for example, reference to "a plasticizer" includes one or more of such plasticizers, and reference to "the method" includes reference to equivalent steps and methods known to those of ordinary skill in the art that could be modified or substituted for the methods described herein.

The term "cellulosic", as used herein, refers to cellulose acetates and cellulose acetate esters and includes, but is not limited to, cellulose acetate, cellulose acetate propionate, and cellulose acetate butyrate. Cellulose acetate esters include, but are not limited to, cellulose diacetate and cellulose triacetates. The term "cellulosic" also includes all hydrates of cellulosics (e.g. anhydrous cellulose acetate, cellulose acetate monohydrate, cellulose acetate dihydrate, cellulose acetate trihydrate, and cellulose acetate tetrahydrate) as well as anhydrous forms of cellulosics.

The term "optimal fragrance intensity", as used herein, refers to a fragrance intensity of scented cellulosic which is obtained using a minimum amount of fragrance for the given fragrance intensity. For example, each point of the Odor Intensity—Fragrance loading curve shown in FIG. 1 that is to the left of Point C (including Point C itself) is an optimal fragrance intensity. In contrast, point B in FIG. 1 is not an optimal fragrance intensity, even though it has the same odor intensity as point A (which is an optimal fragrance intensity), since it is not obtained with a minimum amount of fragrance. If the intensity of the emitted fragrance decreases upon selecting a lower fragrance:plasticizer ratio, then the scented cellulosic has an optimal fragrance intensity. Under these circumstances, the ratio of fragrance:plasticizer can be increased until a fragrance:plasticizer weight ratio is obtained that achieves the maximum fragrance intensity in the scented cellulosic. For purposes of this application, a scented cellulosic with optimal fragrance intensity also has an amount of fragrance that yields an optional fragrance longevity since both intensity and longevity are functions of the diffusion of the fragrance through the cellulosic.

The term "pre-melt cellulosic", as used herein, refers to the unprocessed cellulosic starting material that is to be mixed with a plasticizer and processed with one or more extrusion or processing techniques. The pre-melt cellulosic is provided in solid powdered form with uniform particle distribution, as opposed to a liquid or gel. In preferred embodiments, the pre-melt cellulosic is processed to provide fragranced cellulosics for end-use applications, particularly end-use applications with structural form.

The term "maximum fragrance intensity" as used herein refers to the maximum odor intensity possible for a cellulosic. The maximum fragrance intensity of FIG. 1 is point C.

The term "net plasticizer" refers to all components having a plasticizing effect on cellulosics, and generally refers to the effect of the plasticizer (as that term is traditionally used) plus the fragrance composition, plus the solvent composition.

A "high preliminary fragrance:plasticizer weight ratio" is a weight ratio of fragrance:plasticizer that provides a fragrance intensity does not provide optimal fragrance intensity per unit of fragrance present in the cellulosic. A person of ordinary skill will know that a high preliminary fragrance:plasticizer weight ratio is selected when, upon running a second trial with a lower fragrance:plasticizer weight ratio (e.g., a scented cellulosic with a decreased amount of fragrance), the intensity of the emitted fragrance increases. The term "plasticizer" in the fragrance:plasticizer ratio refers to the weight of traditional plasticizer in the pre-melt cellulosic, and the term fragrance refers to the weight of fragrance in the pre-melt cellulosic.

A "low preliminary fragrance:plasticizer weight ratio" is a weight ratio of fragrance:plasticizer that provides a fragrance intensity that falls below the maximum possible fragrance intensity of a given cellulosic while maximizing the intensity that is achieved per unit of fragrance present in the cellulosic. A person of ordinary skill will know that a low preliminary fragrance:plasticizer weight ratio is selected when, upon running a second trial with a higher fragrance:plasticizer weight ratio (e.g., a scented cellulosic with an increased amount of fragrance), the intensity of the emitted fragrance increases. The term "plasticizer" in the fragrance:plasticizer ratio refers to the weight of traditional plasticizer in the pre-melt cellulosic, and the term fragrance refers to the weight of fragrance in the pre-melt cellulosic.

The term "solvent system" refers to solvents containing a component that possesses both a non-polar entity, such as, but not limited to, a non-polar alkylene chain, and a polar entity such that the component has both a non-polar and polar character. Examples of polar entities within molecules that are included in the solvent system include alcohol, hydroxyl, carboxyl (including carboxyl groups found in organic acids), ester, halogen and primary, secondary and tertiary amine functional groups.

As used herein, the term "soluble" refers to a condition in which a material is dissolved, or substantially dissolved in the given solvent, i.e. the material breaks up into particles (generally single atoms or molecules) that are too small to be seen with the naked eye. Liquid materials are said to be solvent in liquid solvents when the liquid material and liquid solvent combine to form a solution such that the two components are completely miscible or substantially miscible to the naked eye (e.g. including solvents in which the liquid solute forms microcolloids such that the two components appear completely or substantially miscible to the naked eye).

Reference to compounds used herein, including all glycols and glycol ethers described in this application, includes polymers in which the referenced compound forms a subunit. For example, reference to hexylene glycol includes polymers in which hexylene glycol is a monomer in the polymer chain.

As used herein, the term "about" means within 10% of a given value, preferably within 5%, and more preferably within 1% of a given value. Alternatively, the term "about" means that a value can fall within a scientifically acceptable error range for that type of value, which will depend on how precise a measurement can be obtained by the available tools.

All ratios and percentages are given as weight percent or weight ratios unless otherwise noted.

Obtaining Optimal Fragrance Intensity and Longevity

The present application is based, in part, on the discovery that fragranced cellulose acetates and cellulose acetate esters can exude increased fragrance intensity by carefully selecting the fragrance:plasticizer ratio. Surprisingly, it has been found that cellulosics loaded with lower amounts of fragrance oftentimes exhibit more intense fragrance emissions than the same cellulosic loaded with more fragrance. In other words, a fragranced cellulose acetate or cellulose acetate ester having a lower fragrance:plasticizer ratio often has a more intense fragrance emission, after processing, than the counterpart cellulose acetate or cellulose acetate ester with a higher fragrance:plasticizer ratio. It is unexpected that after reaching a maximum odor intensity, the intensity of the cellulosic's fragrance begins to decrease or stabilize as more fragrance is added to the composition.

A concept of the present invention is shown in FIG. 1, which is a prophetic fragrance intensity curve at increasing loading of fragrance. As the loading of fragrance increases, the fragrance intensity increases to a certain point C. Thereafter, the intensity of the fragrance decreases as more fragrance is loaded into the cellulosic.

Points A and B demonstrate a paradox of the present invention. The fragrance weight percent corresponding to point A provides the same odor intensity as the fragrance weight percent corresponding to point B. It is believed that, without benefit of the present invention, most would operate in the region of this curve to the right of point C, in which the "return" per unit of fragrance—the most expensive component of scented cellulosics—is not maximized. Without benefit of the present invention, persons of ordinary skill in the art would assume that increased fragrance loading necessarily provides a cellulosic with increased fragrance intensity. Accordingly, without benefit of the present invention persons of ordinary skill would not select fragrance amounts that are less than or equal to the amount of fragrance that achieves the maximum fragrance intensity (which corresponds to the wt % at point C in FIG. 1), therefore would not optimize the amount of fragrance in the pre-melt cellulosic.

Correlations for diffusion coefficients factor in the "association parameter" of the solvent (see C. R. Wilke, Chem. Eng. Prog., 45:218-224 (1949)) and the "mobility" of the diffusing particle (see Nernst-Einstein equation described in F. Daniels and R. A. Alberty, *Physical Chemistry*, Wiley, New York, p. 650 (1955)). Chapter 16 of *Transport Phenomena*, Bird, Stewart, and Lightfoot (1960) and the above-mentioned technical journals are hereby incorporated by reference. Without being bound to any particular theory, it is believed that there is an optimal ratio of fragrance:plasticizer for a given plasticizer/fragrance combination. When the optimal fragrance:plasticizer ratio is exceeded, it is believed that the association parameter of the solvent changes such that the diffusion of the fragrance through the cellulosic is hindered.

On a more physical level, it is believed that optimized fragrance:plasticizer ratios, and hence, optimized levels of traditional plasticizer better facilitate the formation of channels, continuous voids, or a network of holes, within the processed cellulosic which facilitates the diffusion of the fragrance through the cellulosic. Increased diffusion through the cellulosic facilitates both increased fragrance intensities and increased longevity of the fragrance. In other words, fragrance longevity and fragrance intensity are both a function of the diffusion of fragrance through the cellulosic. Furthermore, in embodiments of the invention that include a solvent system that includes a component that has both a polar or non-polar character (discussed below) the diffusion of the fragrance through the cellulosic is further increased since the fragrance is better distributed throughout the cellulosic and not accumulated into globules.

Also, it has been found that particular plasticizers, including those specifically set forth herein, better facilitate the diffusion, and hence delivery, of fragrance to the ambient atmosphere. Also, pigments, such as opaque color additives like Titanium Dioxide, hinder the diffusion of fragrance through the cellulosic.

Plasticizer and the "Net Plasticizer" Effect

The present invention is also based, in part, on the discovery that a portion of the fragrance, up to and including its entire weight mass, must be considered as an equivalent mass of plasticizer. Similarly, the present invention is also based, in part, on the discovery that a portion of additives including glycols and ethers of glycols described below, up to and including its entire weight mass, must be considered as an equivalent mass of plasticizer. This is because the fragrances and additives have a plasticizing effect in cellulosics in and by themselves. The effect of the plasticizer plus the fragrance and other additives is referred to herein as the net plasticizer effect.

When a person of ordinary skill has determined the amount of plasticizer that will achieve necessary processing parameters in a non-scented cellulosic, one cannot merely add fragrance to this amount of plasticizer and still obtain the same processing parameters. Accordingly, when determining the amount of plasticizer to be added in order to achieve necessary processing parameters, one must account for the plasticizing effect of the added fragrance and additive, such as alkylene glycol and glycol ether. While a certain level of traditional plasticizer is always required to prevent degradation of the pre-melt cellulosic, the addition of fragrance and, for example, glycol or glycol ether additives should be counteracted with a reduction in the amount of traditional plasticizer employed in the scented cellulosic. Conversely, an increase in the amount of traditional plasticizer should be counteracted by a decrease in the amount of fragrance. The present invention is based, in part, on the surprising discovery that a reduction in the amount of fragrance and increase in the amount of traditional plasticizer in the pre-melt cellulosic oftentimes yields processed cellulosics with higher fragrance intensities and increased fragrance longevity.

Therefore, in increasing the amount of fragrance which will yield optimal fragrance intensities, the amount of plasticizer should be decreased in order to obtain similar processing characteristics. Conversely, when decreasing the amount of fragrance, the amount of plasticizer should be increased. In many embodiments of the present invention, an increase or decrease of 1 unit of fragrance is effectively counteracted by a decrease or increase, respectively, of 1 unit of plasticizer (see, e.g., Example 1 below).

The amount of net plasticizer will vary depending on the particular set of physical properties desired, and the particular cellulosic employed. Typical formulations of scented cellulose acetate butyrate may have, for example, between about 4% and 23%, by weight, of net plasticizer. Typical formulations of scented cellulose acetate propionate may have, for example, between about 7% and 18%, by weight, of net plasticizer. Typical formulations of scented cellulose acetate may have, for example, between about 13% and 35%, by weight, of net plasticizer. Generally, the amount of net placticizer is from about 20 wt % to about 40 wt % (e.g., about 30 wt %).

For example, in one embodiment in which the cellulosic is cellulose acetate propionate, the plasticizer is dioctyl adipate (DOA) and a hexylene glycol additive is included, the amount of net plasticizer (DOA+fragrance+hexylene glycol) is from about 20 wt % to about 40 wt %, e.g., about 30 wt %. In a further illustration of this embodiment, the amount of traditional plasticizer is from about 2 wt % to about 35 wt %, or from about 4 wt % to about 35 wt %.

In an alternative embodiment, the cellulosic is cellulose acetate, the plasticizer is diethyl phthalate (DEP), the amount of net plasticizer is also in the range of about 20 wt % to about 40 wt % (e.g., about 30 wt %). In a further aspect of this embodiment, the amount of traditional plasticizer is from about 7 wt % to about 35 wt %, or from about 11 wt % to about 35 wt %.

Examples of plasticizers that can be used in various embodiments of the present invention include, but are not limited to, dibutyl phalate, diethyl phthalate, dimethyl phthalate, triacetin, diethylhexyl-phthalate, and dioctyl phthalate. Also, environmentally sensitive plasticizers can be used, such as plasticizers based on castor oil. These environmentally sensitive plasticizers can be used, for example, as substitutes for phthalate plasticizers. Other plasticizers will present themselves to those of ordinary skill in the art, including those set forth under "Plasticizers" in Volume 19 of the Encyclopedia of Chemical Terminology (4$^{th}$ edition) by Kirk-Othmer, which is hereby incorporated by reference.

Solvent Systems for Plasticizer/Fragrance Components

Components possessing both a non-polar entity and a polar entity are used in solvents to improve the dispersability of the fragrance in the pre-melt cellulosic. In such embodiments, combining the fragrance and the plasticizer with the non-polar/polar solvent system facilitates the migration of the fragrance through the processed cellulosic. Since plasticizers fill the space between polymer strands, the plasticizers form a network of microscopic liquid filled channels throughout and on the surface of the plastic which allows the fragrance to travel and to leach out of the plastic over time. If the fragrance is better dispersed throughout the cellulosic matrix, i.e. not agglomerated into globules which remain encapsulated in the cellulosic, their migration through the matrix over time is facilitated when processed with a solvent system of the present invention.

Generally, solvent systems which are soluble in both a) an alcohol (polar), e.g. ethanol, and b) benzene (non-polar) are included within the solvent systems in embodiments of the present invention. Some examples of solvent systems are solvent systems comprising propylene glycol, hexylene glycol, butyl carbitol and butyl ethylene glycol. Preferably, the solvent systems consists essentially of the component that has a non-polar entity and a polar entity, including solvent systems which consist essentially of a glycol, or a glycol ether, generically, or as described in greater detail below. Accordingly, the solvent system have nonionic characteristics allowing them miscibility in non-polar components (in this case the plasticizer) and available functional (e.g. hydroxyl) groups allowing for hydrogen-bonding with more polar materials (fragrance materials).

While not being bound to any particular theory, it is believed that the addition of this class of solvents possessing non-polar character and available functional groups (e.g. hydroxyl groups) allows for greater long-term migration of fragrance materials via a mechanism in which the fragrance becomes attached (e.g. hydrogen bonded) to the plasticizer. Without the addition of this class of solvents, the plasticizer and fragrance will repel each other much like oil and water, causing the majority of the fragrance to be entrapped/encapsulated in the polymer. With the addition of this class of solvents the plasticizer and the fragrance become effectively one material encompassing a much larger percentage of the overall plastic than just the fragrance alone.

Glycols

In one embodiment of the present invention, a glycol is included in a pre-melt composition for a scented cellulosic, along with a plasticizer and a fragrance component. In one application of this embodiment, the pre-melt composition comprises an alkylene glycol. The glycol may be a $C_3$-$C_{12}$ substituted or unsubstituted alkylene glycol, a $C_4$-$C_{10}$ substituted or unsubstituted alkylene glycol, a $C_5$-$C_7$ substituted or unsubstituted alkylene glycol. Other examples of alkylene glycols in embodiments of the present invention include methylene glycol, ethylene glycol, propylene glycol, butylene glycol, pentylene glycol, hexylene glycol, heptylene glycol, octylene glycol, nonylene glycol, decylene glycol, undecylene glycol, and dodecylene glycol.

In a preferred embodiment, the solvent system comprises, or more preferably, consists essentially of, hexylene glycol. CAS reports that hexylene glycol is a water-white viscous liquid which exhibits slight hydroscopic properties. It is compatible with aromatic hydrocarbons and is miscible with water, fatty acids and low molecular weight alcohols.

Ethers of Glycols

In another embodiment of the present invention, a glycol ether is included in a pre-melt composition for a scented cellulosic, along with a plasticizer and a fragrance component. In one application of this embodiment, the glycol ether is an alkyl ether of alkylene glycol (ethers of alkylene glycol). For example, in embodiments of the present invention, the glycol ether is a $C_1$-$C_{10}$, or a $C_2$-$C_8$, or a $C_3$-$C_5$ mono or poly alkyl ether of an alkylene glycol. In a preferred embodiment, the solvent system includes, or consists essentially of, monoethyl and monobutyl ethers of diethylene glycol (e.g butyl carbitol).

In one embodiment, the alkyl glycol ether is a monoethyl ether, e.g. n-ethyl ether, of an alkylene glycol. In one embodiment, the glycol ether is a pentyl ether of an alkylene glycol, e.g. pentyl ethylene glycol. In another embodiment, the glycol ether is a monobutyl ether, e.g. n-butyl ether of an alkylene glycol (e.g. ethylene glycol). In a preferred embodiment, the alkylene glycol is ethylene glycol, and the ether is n-butyl.

In another embodiment, the alkyl glycol ether is selected from propylene glycol monomethyl ether, dipropylene glycol monomethyl ether and tripropylene glycol monomethyl ether. These alkyl glycol ethers are available from Dow Chemicals under the tradenames Dowanol®PM, Dowanol®DPM, and Dowanol®TPM, respectively. In a preferred embodiment, the solvent system includes, or consists essentially of, dipropylene glycol monomethyl ether.

Effective Amounts of Glycol and Glycol Ether, Traditional Plasticizer, and Cellulosic in Pre-Melt Cellulosic The amount of glycol or glycol ether used in embodiments of the present invention is an amount of glycol or glycol ether that is effective to facilitate the migration of fragrance through the cellulosic. In one embodiment of the present invention, the amount of glycol or glycol ether ranges from about 0.1% to about 33% in the pre-melt composition. In another embodiment, the amount of glycol or glycol ether ranges from about 0.5% to about 20% in the pre-melt composition. In another embodiment, the amount of glycol or glycol ether ranges from about 1% to about 11% in the pre-melt composition. In another embodiment, the amount of glycol or glycol ether ranges about 8% in the pre-melt cellulosic. These amounts of glycol or glycol ether are in weight percent, based on the total weight of the pre-melt cellulosic.

In one embodiment of the present invention, the amount of cellulosic ranges from about 48 wt %-93 wt %, the amount of glycol or glycol ether ranges from about 0 wt % to about 12 wt %, the amount of fragrance ranges from about 1% to about 30%, and the amount of traditional plasticizer ranges from about 2 wt % to about 35 wt %. In an alternative embodiment, the amount of cellulosic ranges from about 60 wt % to about 80 wt %, the amount of glycol or glycol ether ranges from about 3% to about 10 wt %, the amount of fragrance ranges from about 10 wt % to about 25 wt % and the amount of traditional plasticizer ranges from about 10 wt % to about 25 wt %. It is imperative that the pre-melt composition contain enough cellulosic such that the pre-melt composition is in powder from, as opposed to a gel or liquid. Therefore, the minimum amount of cellulosic contained in the pre-melt composition is generally at least about 40 wt % of the total weight of the pre-melt cellulosic, or in another embodiment, above about 48 wt % of the total weight of the pre-melt cellulosic.

Modification of Net Plasticizer Amount

Higher net plasticizer amounts should be selected for projects which require a softer melt flow upon processing the cellulosic. For example, for an end use applications such as a thin film for packaging, the amount of net plasticizer can be around 25%; whereas for a decorative mask end use that is desired to be softer, the amount of net plasticizer can be around 40%. Depending on the desired fragrance intensity of the end use product, the relative amount of fragrance is selected so as to provide a scented cellulosic with optimal fragrance intensity according to the process of the present invention. The fragrance, glycol and/or amount of plasticizer are each selected to account for the residual amount of net plasticizer upon optimization of the amount of fragrance according to the process of the present invention.

Processing Techniques

Before any processing techniques are employed, an amount of plasticizer is added to the pre-melt cellulosic to prevent degradation upon heating. Fragrance, and other additives such as alkylene glycols or glycol ethers may be added with the plasticizer, or more preferably, after an initial amount of plasticizer has already been added to the pre-melt cellulosic. In the preferred two-step process, the plasticizer is first added to the pre-melt cellulosic and, once the mixture is visibly dry (meaning the liquid plasticizer has absorbed into the interior of the cellulose ester powder particle), the fragrance is then dispersed over the powder. The plasticizer which has been already absorbed into the powder acts as a receptor to the fragrance and helps it migrate into the particles of the pre-melt cellulosic.

As described above, the plasticizer and fragrance—which also acts as a plasticizer—together form the "net plasticizer". The introduction of a fragrance into the cellulosic requires a mixing step such that the fragrance is sufficiently dispersed throughout the pre-melt cellulosic. The pre-melt cellulosic can then be processed into solid pellets by techniques known to those of ordinary skill in the art, non-limiting examples of which are described below:

(a) Single-Screw Compounding (SSC)—SSC requires a separate heating, agitation, and mixing step to combine a compatible pre-heated liquid plasticizer in appropriate proportions, possibly with colorants, stabilizers, and additives with the pre-melt cellulosic. Heat is required both for the powder and for the plasticizer to aid in its absorption into the interior of each powder particle. Constant agitation of the powder is required to ensure that both the heat being introduced and the additives are being uniformly distributed. The liquid additives will absorb into the powdered polymer, and any dry powder additives must be evenly dispersed throughout the blend of materials. The final mixed materials are then processed through a plastics extrusion melt process, which imparts to the materials sufficient heat and pressure to plasticate the polymer. The extrudate is then pushed from the extruder through a die into a multitude of strands. The strands are subsequently cut into pellets, which can subsequently be processed through other secondary melt processes into various end products.

(b) Twin-Screw Compounding (TSC)—TSC extruders offer the ability to eliminate the dry-mixing step necessary for SSC. While the same mixing steps can be used prior to introduction of the entire mixture into a twin-screw extruder for plasticating and then pelletizing the materials, it is possible to introduce all of the components into various stages of a twin-screw compounding extruder without prior mixing. As in SSC, the fragrance can be either added in combination with the plasticizer, or it can be introduced in a second step.

(c) Solvent casting—Cellulose esters, including cellulose diacetate and cellulose triacetate are used as cellulosics in various embodiments of the present invention. Cellulose esters may be processed into thin films using solvent casting techniques known to a person of ordinary skill in the art. For example, the cellulose ester may be dissolved in a solvent such as acetone or methylene chloride to prepare a viscous dope. Standard plasticizer may be added to the viscous dope and processed onto a substrate, such as polished stainless steel or chrome. When the solvent evaporates it leaves a remaining, preferably uniform, film of plasticized cellulose ester film.

Upon control of concentration, pressure, temperatures, feed rates, evaporation rates, etc., solvent casting techniques can be used to provide scented cellulosics for an end use application. This technique is conducive to fragranced cellulosic applications due to the relative low processing temperatures, as compared to other techniques such as melt-extrusion. For example, solvent casting techniques can be used in embodiments of the present invention to prepare scented cellulosics with optimal fragrance intensity, and/or a scented cellulosic with an alkylene glycol or alkylene glycol ether of the present invention.

(d) Secondary Melt-Processing—Once processed into solid pellet form, the fragranced cellulosics are then processed into an end-use application by means of a secondary melt-processing step. Non-limiting examples of secondary melt-processing steps include compression molding, injection molding, casting and extrusion. Secondary Melt-Processing Techniques are described in Chapter XV of "Methods of Processing and Fabrication", Handbook of Plastics, Ninth Printing (1943), which is hereby incorporated by reference in its entirety.

Determining Initial Fragrance Intensities and Fragrance Longevity

Fragrance intensities and fragrance longevity can be determined by persons of ordinary skill in the art. For example, fragrance intensities of a sample of products can be rated on a scale by a panel of individuals trained to ascertain the intensity of the fragrance subjectively perceived by the panel members. Preferably the test is performed in a controlled environment devoid of smells that could influence the results, and the panel is not informed of the contents of the samples to avoid bias. Further information regarding measuring fragrance intensities can be found, for example in ASTM Standard E 544-99, "Standard Practices for Referencing Suprathreshold Odor Intensity; which is hereby incorporated by reference in its entirety.

Similarly, fragrance longevities can be determined by person's of ordinary skill in the art. For purposes of this application, fragrance longevity can be defined as the period of time in which a composition retains at least 50% of its initial fragrance. Alternatively, longevity can be measured based on the period of time in which the composition retains a perceivable fragrance. Again, the perception of fragrance is preferably carried out by person's trained in art (e.g., "noses") and in a fragrance-controlled environment.

End-Use Applications

Various end-use applications are possible and within the scope of the present application. While it is preferred that such end-use applications for scented cellulosics have optimal fragrance intensity, including maximum fragrance intensities, and/or being processed with, and hence containing, a solvent system as described above, the end-use applications discussed below can be prepared using any process to prepare scented cellulosic formulations.

In embodiments of the present invention, end uses prepared from the solid pellets of the present invention have a structural form, for example, flexible sheets, containers, and solid objects such as cell phone holsters or the outer casing for the cell phone itself.

Non-limiting examples of end-use applications include jewelry and personal accessories including, but not limited to, bangles, bracelets, necklaces, earrings, pendants, ankle bracelets, facial jewelry such as nose, lips and eyebrow rings and studs, headbands, belt buckles, buttons, barrettes, hair bands, hair clips, bobby pins, zippers, pocket protectors, thimbles, rubber bands, including rubber bands used to bind hair, clothing stays & clasps, shoelace caps, bands for use with wristwatches and shoulder bags, holsters for cell phones, money clips, change holders, purses, wallets, sunglasses and eyeglasses cords, eyewear, such as frames for glasses, razor handles, hair accessories, hairbrush handles, toothbrushes handles, toothbrush holders, cases, computer mice, calculator cases, telephone headsets, packaging tape, and ribbons.

Other examples of end-use applications include keychains, promotional items for fragrance companies to replace, for example, scent strips, packaging and/or containers for hand sanitizers and fragrance products, including perfume, cologne, and after shave, cellowrap, credit cards, gift cards, artificial flowers and plants, bottle caps, binder clips, automobile air fresheners, shower curtain rings, shower curtains, bathroom garbage cans, toothbrushes, headsets for phones, razor handles, splints for inclusion in first-aid kits, soap holders, sachets, hair accessories, hangers, including clothes hangers, shoe horns, shoe trees, sunglasses, learning tools for kids, toys for kids (e.g. play kitchen sets with scented pizza, corn) and replacements for scratch-and-sniff books, cigarette lighters, and inserts for greeting cards.

As non-limiting examples of interior and household accents, the process of present invention can be used to prepare pen holders, pen cases, soap dishes, table decorations, vases, desk ornaments, candle holders, decorative non-burning candles, clothespins for hanging laundry, napkin, toilet paper, and paper towel dispensers, television remote control casings, cases for clocks, picture frames, bathtub toys such as floating ducks, makeup and compact cases, lunch boxes, cutting boards, lamp shades, telephones, refrigerator magnets, dish drains, letter holders, placemats, cases for personal products such as pill reminder cases, dental floss, and retainers, air fresheners, auto trim, drawer sachets, plates, cups, spoons, forks, other utensils involved in food preparation, pots for indoor plants, material for Venetian blinds, salt and pepper shakers, condiment holders, food storage devices, and garbage cans and lids. These products can also be prepared by other processes for preparing scented cellulosics.

Point of purchase applications that can be prepared by the process of the present invention include, but are not limited to, packaging components such as fragrance displays to replace spritzing, tubes, cellowrap, caps, trim, display components such as rails and trim, including promotional display advertisements directed to personal care products such as deodorants, mouthwash, and flavored pharmaceutical products, including cough suppressants, sore throat lozenges or sprays, pain reducers, fever reducers, vitamins, antibiotics, and cold and influenza medications. Other end-use products include, containers with fragrances similar to the product contained within, mailing products used to store and transport clothes, and security tags for stores. Another set of uses include devices and components used for transferring scent to clothing, such as hangers, shoe horns, shoe trees, sachets, clothing inlays, and protective wrap for products.

The process of the present invention can also be used to prepare, for example, animal lures, animal toys, and insect repellents, such as mouse traps, rodent traps, roach "motels", animal attractants, including accessories for hunters, animal repellants, including ornamental lawn furniture or tomato or garden stakes that have fragrances that repel deer and other wildlife, fishing lures, toys for household pets, such as gnawable artificial food or toys, fake play rodents such as a pretend mouse, collars, balls, frisbees, and other "fetchable" objects, scented poles to attract and capture insects, and artificial moth balls.

The following examples illustrate the present invention without limitation.

EXAMPLE 1

A series of formulations of fragranced cellulose acetate proprionate with a proprietary pina colada fragrance and Dioctyl Adipate (DOA) having varying fragrance:plasticizer ratios were prepared as shown below:

| Sample | Wt % Fragrance | Wt % Plasticizer | Net Plasticizer- wt % | Fragrance: Plasticizer Ratio |
|---|---|---|---|---|
| 1 | 5 | 5 | 10 | 1 |
| 2 | 6 | 4 | 10 | 1.5 |
| 3 | 7 | 3 | 10 | 2.33 |
| 4 | 8 | 2 | 10 | 4 |

Ten individuals were asked to rank the samples on the basis of strength of scent level. The identify of the samples were not identified to the panel.

Sample 1, containing a fragrance:plasticizer ration of 1 was judged by all 10 panelist to have the strongest fragrance. Sample 4, which contains four-fold increase in fragrance: plasticizer ratio, was judged by all 10 panelist to be the weakest fragrance. All four samples did not exhibit processing problems due to insufficient plasticizer amount.

EXAMPLE 2

The following pre-melt cellulosic compositions were prepared:

| Amount of Net Plasticizer (wt %) | Amount of Traditional Plasticizer (wt %) | Type of Traditional Plasticizer (wt %) | Type of Cellulosic | Amount of Cellulosic (wt %) | Amount of Fragrance (wt %) | Amount of Hexylene Glycol |
|---|---|---|---|---|---|---|
| 33% | 8.10% | DEP | CA | 67.00% | 19.30% | 5.60% |
| 33% | 10% | DEP | CA | 67.00% | 15% | 8% |
| 33% | 10% | DEP | CA | 67.00% | 15% | 8% |
| 33% | 8% | DEP | CA | 67.00% | 19% | 6% |
| 33% | 13% | DEP | CA | 67.00% | 20% | 0% |
| 33% | 10% | DEP | CA | 67.00% | 17% | 6% |
| 33% | 15% | DEP | CA | 67.00% | 18% | 0% |
| 27% | 14.2% | DEP | CA | 73.30% | 10% | 2.4% |
| 33% | 10% | DEP | CA | 67.00% | 15% | 8% |

-continued

| Amount of Net Plasticizer (wt %) | Amount of Traditional Plasticizer (wt %) | Type of Traditional Plasticizer | Type of Cellulosic | Amount of Cellulosic (wt %) | Amount of Fragrance (wt %) | Amount of Hexylene Glycol |
|---|---|---|---|---|---|---|
| 33.70% | 9% | DEP | CA | 66.30% | 18% | 6% |
| 29.40% | 8% | DEP | CA | 70.60% | 15% | 6% |
| 35% | 11% | DEP | CA | 65.00% | 18% | 6% |
| 33% | 15% | DEP | CA | 67.00% | 18% | 0% |
| 33% | 10% | DEP | CA | 67.00% | 15% | 8% |
| 33% | 10% | DEP | CA | 67.00% | 15% | 8% |
| 33% | 10% | DEP | CA | 67.00% | 15% | 8% |
| 35.50% | 12% | TRI | CA | 64.50% | 18% | 6% |
| 35.50% | 18% | TRI | CA | 64.50% | 18% | 0% |
| 33.70% | 9% | DOA | CAP | 66.30% | 18% | 6% |
| 29.40% | 8% | DOA | CAP | 70.60% | 15% | 6% |
| 32.50% | 16.50% | DEP | CA | 67.50% | 10% | 6% |
| 41% | 13% | TRI | CA | 59.00% | 22% | 6% |
| 36% | 11.30% | DEP | CA | 64.00% | 19% | 6% |
| 33.30% | 11.40% | DEP | CA | 66.70% | 18.90% | 3% |
| 38% | 13.20% | DEP | CA | 62.00% | 19% | 5.80% |
| 36% | 14.50% | TRI | CA | 64.00% | 15% | 6.80% |
| 35.30% | 13.20% | DEP | CA | 64.70% | 16.70% | 5.40% |
| 36% | 14.70% | DEP | CA | 64.50% | 15% | 5.90% |
| 14% | 3.90% | DOA | CAP | 86.00% | 10% | 0.00% |
| 33.50% | 16.40% | DEP | CA | 66.50% | 10% | 7.10% |
| 39.50% | 16.60% | DEP | CA | 60.50% | 18.10% | 6.40% |
| 33.60% | 16.60% | DEP | CA | 66.40% | 10% | 7% |
| 38.60% | 14.90% | DEP | CA | 61.40% | 23.70% | 0% |
| 38.60% | 14.90% | DEP | CA | 61.40% | 19.10% | 4.70% |
| 38.60% | 14.90% | DEP | CA | 61.40% | 23.70% | 0% |
| 38.60% | 14.90% | DEP | CA | 61.40% | 19.10% | 4.70% |
| 38% | 16% | DEP | CA | 62.00% | 17% | 5% |
| 37.70% | 17.90% | DEP | CA | 62.30% | 19.80% | 0% |
| 38.00% | 15.00% | DEP | CA | 62.00% | 17% | 6% |
| 35.30% | 13.20% | DEP | CA | 64.70% | 16.70% | 5.40% |
| 39.50% | 14.90% | DEP | CA | 60.50% | 18.10% | 6.40% |
| 29.50% | 8.5% | DEP | CA | 70.50% | 15% | 6% |
| 37% | 15.5% | DEP | CA | 62.60% | 17% | 5% |
| 37% | 15.5% | DEP | CA | 62.60% | 17% | 5% |
| 37% | 15.5% | DEP | CA | 62.60% | 17% | 5% |
| 33.50% | 16.40% | DEP | CA | 66.50% | 10% | 7.10% |
| 37.40% | 15.50% | DEP | CA | 62.60% | 17% | 5% |
| 14% | 9.5 | DOA | CAP | 86.00% | 4.4% | 0% |
| 34% | 16 | DEP | CA | 66.00% | 12.50% | 5.50% |
| 34% | 16 | DEP | CA | 66.00% | 12.50% | 5.50% |
| 33.50% | 16.40% | DEP | CA | 66.50% | 10% | 7.10% |
| 39.50% | 16.88% | DEP | CA | 60.50% | 18.10% | 6.40% |
| 33.30% | 18.20% | DEP | CA | 66.70% | 10% | 5.10% |
| 14% | 9.50% | DOA | CAP | 86.00% | 4.40% | 0% |
| 34% | 16% | DEP | CA | 66.00% | 12.50% | 5.50% |
| 34% | 16% | DEP | CA | 66.00% | 12.50% | 5.50% |
| 38.50% | 15.40% | DEP | CA | 61.50% | 18% | 5.10% |
| 38.50% | 15.40% | DEP | CA | 61.50% | 18% | 5.10% |
| 38.50% | 15.40% | DEP | CA | 61.50% | 18% | 5.10% |
| 35.50% | 17.50% | DEP | CA | 64.50% | 12.50% | 5.50% |
| 35.50% | 17.50% | DEP | CA | 64.50% | 12.50% | 5.50% |
| 35.50% | 17.50% | DEP | CA | 64.50% | 12.50% | 5.50% |
| 35.50% | 17.50% | DEP | CA | 64.50% | 12.50% | 5.50% |
| 35.50% | 23% | DEP | CA | 64.50% | 12.50% | 0.00% |
| 18.30% | 10.00% | DOA | CAP | 81.70% | 10% | 0% |
| 32.90% | 20.30% | DEP | CA | 67.10% | 2.50% | 10.10% |
| 32.90% | 20.30% | DEP | CA | 67.10% | 2.50% | 10.10% |
| 34% | 16% | DEP | CA | 66.00% | 12.50% | 5.50% |
| 34% | 16% | DEP | CA | 66.00% | 12.50% | 5.50% |
| 33.50% | 16.40% | DEP | CA | 66.50% | 10% | 7.10% |
| 37% | 16% | DEP | CA | 63.00% | 15% | 6% |
| 32.90% | 23% | DEP | CA | 67.10% | 10% | 0% |
| 32.90% | 23% | DEP | CA | 67.10% | 10% | 0% |
| 14.50% | 9.50% | DOA | CAP | 85.50% | 5% | 0% |
| 19% | 7% | DOA | CAP | 81.00% | 10% | 2% |
| 14.50% | 11.50% | DOA | CAP | 85.50% | 3% | 0% |
| 25.30% | 7.30% | DOA | CAP | 74.70% | 15% | 3% |
| 14% | 9.50% | DOA | CAP | 86.00% | 4.40% | 0% |
| 38.50% | 15.40% | DEP | CA | 61.50% | 18% | 5.10% |
| 38.50% | 15.40% | DEP | CA | 61.50% | 18% | 5.10% |
| 32.50% | 16.90% | DEP | CA | 67.50% | 10% | 5.60% |
| 32.50% | 16.90% | DEP | CA | 67.50% | 10% | 5.60% |
| 35.50% | 17.50% | DEP | CA | 64.50% | 12.50% | 5.50% |

-continued

| Amount of Net Plasticizer (wt %) | Amount of Traditional Plasticizer (wt %) | Type of Traditional Plasticizer (wt %) | Type of Cellulosic | Amount of Cellulosic (wt %) | Amount of Fragrance (wt %) | Amount of Hexylene Glycol |
|---|---|---|---|---|---|---|
| 29.50% | 8.5% | DEP | CA | 70.50% | 15% | 6.0% |
| 34.00% | 10.0% | DEP | CA | 66.00% | 14% | 10% |
| 29.50% | 14.5% | DEP | CA | 70.50% | 15% | 0% |
| 34.00% | 20.0% | DEP | CA | 66.00% | 14% | 0% |
| 20.70% | 8.80% | DOA | CAP | 79.30% | 11% | 1% |
| 24% | 8.5% | DOA | CAP | 76.50% | 15% | 0% |
| 36.30% | 16.00% | DEP | CA | 63.70% | 15% | 5.30% |
| 32.70% | 20.40% | DEP | CA | 67.30% | 2.10% | 10.10% |
| 38.50% | 15.40% | DEP | CA | 61.50% | 18% | 5.10% |
| 38.50% | 15.40% | DEP | CA | 61.50% | 18% | 5.10% |
| 36.30% | 16.00% | DEP | CA | 63.70% | 15% | 5.30% |

Types of traditional plasticizer used include diethyl phthalate (DEP); triacetin (TRI); and dioctyl adipate (DOA). Types of cellulosics include cellulose acetate (CA) and cellulose acetate propionate (CAP).

The above pre-melt formulations were processed via either a laboratory roll-mill, and/or using single-screw melt-extrusion compounding. Packaging components, point-of-purchase display components, thin films for packaging, jewelry; air fresheners; and promotional items were prepared.

EXAMPLE 3

A 0.003" thick fragranced film of cellulose acetate is prepared for a packaging end use application. As a "hard" melt flow is desired, the target wt % net plasticizer for the pre-melt cellulosic is 27%. The desired fragrance is inherently a relatively strong fragrance, and a "medium" fragrance intensity on the film is desired. An initial fragrance target of 10% is chosen. A hexylene glycol level of 2.5% is chosen to allow a residual level of 14.5% traditional plasticizer in the formulation.

EXAMPLE 4

A molded decorative desk ornaments, approximately 2 inches thick utilizing cellulose acetate is prepared. A "soft" melt flow is desired. The target wt % net plasticizer for this application is 38%. The desired fragrance is a subtle fragrance, and a strong fragrance intensity is desired. A fragrance target of 16% is chosen. A Hexylene Glycol level of 8% is chosen to allow a residual traditional plasticizer level of 14% in the formulation.

EXAMPLE 5

Pre-melt compositions of cellulose acetate, diethyl phthalate plasticizer, proprietary fruit punch fragrance and hexylene glycol in the amounts shown below were processed into pellets and their fragrance intensity was rated by an observer:

| wt % Traditional Plasticizer | wt % Fragrance | Fragrance: Plasticizer Ratio | wt % hexylene glycol | Fragrance Intensity | Fragrance Longevity |
|---|---|---|---|---|---|
| 8.8 | 19 | 2.16 | 6 | Very Weak | 15 days |
| 11.5 | 19 | 1.65 | 6 | Strong | 60+ days |
| 11.5 | 19 | 1.65 | 3 | Medium | 45 days |
| 13 | 19 | 1.46 | 6 | Strong | 60+ days |
| 13 | 20 | 1.54 | 0 | Strong | 60 days |
| 16 | 17 | 1.06 | 0 | Medium/Strong | 40 days |
| 18 | 15 | 0.83 | 0 | Medium | 30 days |

It is noted that initial fragrance intensity is related to fragrance longevity, i.e., increased initial fragrance intensities yield longer-lasting fragrances and samples with lower initial fragrance intensities yield samples in which the fragrance does not last as long.

The above mentioned patents, patent applications, patent publications, test methods, and publications are hereby incorporated by reference in their entirety.

Many variations of the present invention will suggest themselves to those skilled in the art in light of the above detailed description. All such obvious variations are within the fully intended scope of the invention.

What is claimed is:

1. A process for preparing a scented cellulosic with optimal fragrance intensity, comprising the steps of: (a) determining an amount of net plasticizer to be added to a pre-melt cellulosic composition; (b) selecting a high preliminary fragrance:plasticizer weight ratio of the net plasticizer, wherein the high preliminary fragrance:plasticizer weight ratio is 2 or higher; (c) adding the net plasticizer with the high preliminary fragrance:plasticizer ratio; (d) determining the fragrance:plasticizer weight ratio of net plasticizer that achieves maximum fragrance intensity in the processed scented cellulosic by decreasing the fragrance:plasticizer ratio of the net plasticizer in iterative trials, while the amount of the net plasticizer remains constant over the iterative trials; (e) selecting a final fragrance:plasticizer ratio based on the desired fragrance intensity of the scented cellulosic, wherein the final fragrance:plasticizer ratio is less than or equal to the fragrance:plasticizer ratio in step (d) that achieves the maximum fragrance intensity; and (f) preparing the pre-melt cellulosic composition having the final fragrance:plasticizer ratio.

2. The process of claim 1, wherein the high preliminary fragrance:plasticizer weight ratio is 4 or higher.

3. The process of claim 1, wherein the final fragrance:plasticizer ratio is approximately equal or equal to the fragrance:plasticizer ratio in step (d) that achieves the maximum fragrance intensity.

4. The process of claim 1, wherein the pre-melt composition comprises a scented cellulosic composition including a cellulosic; a plasticizer; a fragrance component; and a glycol or glycol ether, wherein the glycol is a $C_3$-$C_{12}$ substituted or unsubstituted alkylene glycol or a poly($C_3$-$C_{12}$ substituted or unsubstituted alkylene glycol).

5. The process of claim 1, wherein the net plasticizer comprises an amount of plasticizer and an amount of fragrance and the process further includes the steps of:
   adding an amount of plasticizer to a pre-melt cellulosic that is part of the pre-melt composition to prevent degradation upon heating and form a mixture; and
   adding an amount of fragrance to the mixture, which is in powder form, after the mixture is visibly dry as a result of the plasticizer being absorbed into an interior of the cellulosic, wherein the plasticizer that has been absorbed acts as a receptor to the fragrance and helps it migrate into particles of the pre-melt cellulosic.

6. The process of claim 1, wherein the scented cellulosic comprises a pre-melt cellulosic that can be melt processed into a solid end product.

7. A process for preparing a scented cellulosic with optimal fragrance intensity, comprising the steps of: (a) determining an amount of net plasticizer to be added to a pre-melt cellulosic composition; (b) selecting a high preliminary fragrance:plasticizer weight ratio of the net plasticizer, wherein the high preliminary fragrance:plasticizer weight ratio is 2 or higher; (c) adding the net plasticizer with the high preliminary fragrance:plasticizer ratio; (d) determining the fragrance:plasticizer weight ratio of net plasticizer that achieves maximum fragrance intensity in the processed scented cellulosic by decreasing the fragrance:plasticizer ratio of the net plasticizer in iterative trials, while the amount of the net plasticizer remains constant over the iterative trials, wherein the maximum fragrance intensity is an intensity value at which an increase in the fragrance:plasticizer weight ratio, while the net plasticizer amount is held constant, results in the pre-melt cellulosic composition having a fragrance that is less intense; (e) selecting a final fragrance:plasticizer ratio based on the desired fragrance intensity of the scented cellulosic, wherein the final fragrance:plasticizer ratio is less than or equal to the fragrance:plasticizer ratio in step (d) that achieves the maximum fragrance intensity; and (f) preparing the pre-melt cellulosic composition having the final fragrance:plasticizer ratio by an extrusion process to form scented solid pellets that are suitable for a later secondary melt processing step to create an end product having a form different than the scented solid pellet.

8. A process for preparing a scented cellulosic with optimal fragrance intensity, comprising the steps of: (a) determining and selecting an amount of net plasticizer to be added to a pre-melt cellulosic composition in order to subsequently produce an end product having desired properties; (b) determining the fragrance:plasticizer weight ratio of the net plasticizer that achieves maximum fragrance intensity for the selected amount of net plasticizer, wherein the amount of net plasticizer is constant and the maximum fragrance intensity is an intensity value at which an increase in the fragrance:plasticizer weight ratio, while maintaining the constant net plasticizer amount, results in the pre-melt cellulosic composition having a fragrance that is less intense; and (c) preparing the pre-melt cellulosic composition having the maximum fragrance:plasticizer ratio by an extrusion process to form scented solid pellets that are suitable for a later secondary melt processing step to form the end product having a form different than the scented solid pellet.

9. The process of claim 8, wherein the pre-melt composition comprises a scented cellulosic composition including a cellulosic; a plasticizer; a fragrance component; and a glycol or glycol ether, wherein the glycol is a $C_3$-$C_{12}$ substituted or unsubstituted alkylene glycol or a poly($C_3$-$C_{12}$ substituted or unsubstituted alkylene glycol).

* * * * *